United States Patent [19]

Fortney et al.

[11] Patent Number: 5,505,943
[45] Date of Patent: *Apr. 9, 1996

[54] COMPOSITIONS CONTAINING PROTEASE PRODUCED BY VIBRIO AND METHOD OF USE IN DEBRIDEMENT AND WOUND HEALING

[75] Inventors: Donald Z. Fortney, Westminister; Donald R. Durham, Gaithersburg, both of Md.

[73] Assignee: W. R. Grace & Co.-Conn., New York, N.Y.

[ * ] Notice: The term of this patent shall not extend beyond the expiration date of Pat. No. 5,145,681.

[21] Appl. No.: 483,170

[22] Filed: Jun. 7, 1995

Related U.S. Application Data

[63] Continuation of Ser. No. 86,465, Jul. 6, 1993, abandoned, which is a continuation of Ser. No. 670,612, Mar. 13, 1991, abandoned, which is a continuation-in-part of Ser. No. 567,884, Aug. 15, 1990, Pat. No. 5,145,681.

[51] Int. Cl.$^6$ ..................... A61K 38/48
[52] U.S. Cl. .............. 424/94.63; 435/220; 435/909; 935/10; 935/14
[58] Field of Search .............. 424/94.63, 94.64; 435/220, 221; 536/23.2

[56] References Cited

U.S. PATENT DOCUMENTS

| | | | |
|---|---|---|---|
| 3,409,719 | 11/1968 | Noe et al. | 424/94.67 |
| 3,677,900 | 7/1972 | Merkel | 435/220 |
| 4,276,281 | 6/1981 | Crikelair | 424/94.64 |
| 4,329,430 | 5/1982 | Klein et al. | 435/219 |
| 4,668,228 | 5/1987 | Bolton et al. | 604/307 |
| 4,865,983 | 9/1989 | Durham | 435/264 |
| 5,145,681 | 9/1992 | Fortney et al. | 424/94.63 |

OTHER PUBLICATIONS

Imanaka et al. (1968) Nature 324: 695–697.
Merkel et al., "Proteolytic Activity and General Characteristics of a Marine Bacterium, Aeromonas Proteolytica SP. N.," Journal of Bacteriology (1964) 87:1227–1233.
Prytz et al., "The Digestion of Human Burn Eschar by Proteolytic Enzymes," Enzymalia (1965) 28:367–376.
Boxer et al., "Debridement of Dermal Ulcers and Decubiti with Collagenese," Geriatrics (1969) 75–86.
Silverstein et al., "Laboratory Evaluation of Enzymatic Burn Wound Debridement In Vitro and In Vivo," Surgical Forum (1972) 31–33.
Silverstein et al., "In Vitro Evaluation of Enzymatic Debridement of Burn Wound Eschar," Surgery (1973) 73:15–22.
Harris et al., "The Effect of Travase on Wound Healing," Texas Reports on Biology and Medicine (1973) 31:771–776.
Merkel et al., "Collagenolytic Activity of Some Marine Bacteria," Applied Microbiology (1975) 29:145–151.
Pennisi et al., "The Combined Efficacy of Travase and Silver Sulphadizine in the Acute Burn," Burns (1976) 169–172.
Wilkes et al., "Aeromonos Neutral Proteases," Methods in Enzymology (1976) 33:404–415.
Coopwood, "Evaluation of a Topical Enzymatic Debridement Agent," Southern Medical Journal (1976) 69:834–836.
Shakespeare et al., "The Activity of the Enzymatic Debridement Agent Travase towards a Variety of Protein Substrates," Burns (1978) 6:15–20.
Merkel et al., "Purification and Characterization of a Marine Bacterial Collagenase," Biochemistry (1978) 17:2857–2863.
Dreisbach et al., "Induction of Collagenase Production in Vibrio B–30", Journal of Bacteriology (1978) 135:521–527.
Levick et al., "Treatment of Full-Thickness burns with Travase; Results of a Clinical Trial," Burns (1978) 4:281–284.
Falces, "Enzymes for Debridement," Western Journal of Medicine (1980) 133:59–60.
Silverstein et al., "Enzymatic and Nonsurgical Debridement," Journal of Burn Care Rehabilitation (1981) 49.
Makepeace, "Enzymatic Debridement of Burns," Burns (1982) 9:153–157.
Buckman et al., "A Unifying Pathogenic Mechanism in the Etiology of Intraperitoneal Adhesion", J. of Surg. Res. (1976) 20:1–5.
Nierman, "Treatment of Dermal and Decubitus Ulcers," Drugs (1978) 15:226–230.
Ellis, "The Causes and Prevention of Intestinal Adhesions," Br. J. Surg. (1982) 69:241–243.
Holtz, "Prevention and Management of Peritoneal Adhesions," Ferility and Sterility (1984) 41:497–507.
Doody et al., "Recombinant Tissue Plasminogen Activator Reduces Adhesion Formation in a Rabbit Uterine Horn Model," Fertility and Sterility (1989) 51:509–512.

*Primary Examiner*—Robert A. Wax
*Assistant Examiner*—Gabriele E. Bugalsky
*Attorney, Agent, or Firm*—Howard J. Troffkin

[57] ABSTRACT

Compositions and methods of use are provided for debriding and wound healing applications. The compositions contain certain proteases produced by microorganisms of the genus Vibrio

39 Claims, 7 Drawing Sheets

```
TTTAATTTCT GATTTATCAG TAGTTAAACA ACGATTGAAA ATAATCTCCA GGATTGAGAA              60

ATG AAT AAA ACA CAA CGT CAC ATC AAC TGG CTG CTG GCT GTT AGC GCG              108
Met Asn Lys Thr Gln Arg His Ile Asn Trp Leu Leu Ala Val Ser Ala
 1           5                  10                 15

GCA ACT GCG CTA CCT GTC ACC GCT GCA GAA ATG ATC AAC GTA AAT GAT              156
Ala Thr Ala Leu Pro Val Thr Ala Ala Glu Met Ile Asn Val Asn Asp
             20                 25                 30

GGC AGC CTG CTA AAC CAG GCT CTT AAA GCT CAG TCA CAG AGC GTT GCC              204
Gly Ser Leu Leu Asn Gln Ala Leu Lys Ala Gln Ser Gln Ser Val Ala
         35                 40                 45

CCG GTG GAA ACC GGA TTC AAA CAA ATG AAA CGA GTT GTT TTG CCA AAT              252
Pro Val Glu Thr Gly Phe Lys Gln Met Lys Arg Val Val Leu Pro Asn
     50                 55                 60

GGC AAA GTG AAA GTT CGT TAT CAA CAA ACT CAC CAC GGT CTA CCG GTT              300
Gly Lys Val Lys Val Arg Tyr Gln Gln Thr His His Gly Leu Pro Val
 65                 70                 75                 80

TTC AAC ACC TCG GTA GTG GCG ACT GAA TCG AAG TCT GGT AGT AGC GAA              348
Phe Asn Thr Ser Val Val Ala Thr Glu Ser Lys Ser Gly Ser Ser Glu
                 85                 90                 95

GTG TTC GGT GTG ATG GCT CAG GGT ATC GCA GAC GAC GTG TCT ACA CTG              396
Val Phe Gly Val Met Ala Gln Gly Ile Ala Asp Asp Val Ser Thr Leu
             100                105                110

ACG CCA TCC GTT GAG ATG AAG CAG GCC ATT TCA ATT GCT AAA TCG CGT              444
Thr Pro Ser Val Glu Met Lys Gln Ala Ile Ser Ile Ala Lys Ser Arg
         115                120                125

TTC CAA CAG CAA GAA AAA ATG GTT GCG GAA CCT GCA ACG GAA AAC GAA              492
Phe Gln Gln Gln Glu Lys Met Val Ala Glu Pro Ala Thr Glu Asn Glu
     130                135                140

AAA GCC GAG TTG ATG GTT CGT CTG GAC GAC AAC AAT CAA GCG CAA CTA              540
Lys Ala Glu Leu Met Val Arg Leu Asp Asp Asn Asn Gln Ala Gln Leu
145                150                155                160

GTG TAT CTG GTT GAT TTC TTC GTT GCC GAG GAT CAC CCA GCG CGT CCT              588
Val Tyr Leu Val Asp Phe Phe Val Ala Glu Asp His Pro Ala Arg Pro
                 165                170                175

TTC TTT TTC ATT GAT GCG CAA ACG GGT GAA GTA CTG CAA ACT TGG GAT              636
Phe Phe Phe Ile Asp Ala Gln Thr Gly Glu Val Leu Gln Thr Trp Asp
             180                185                190

GGT CTG AAC CAT GCA CAA GCT GAC GGT ACT GGC CCT GGC GGT AAC ACC              684
Gly Leu Asn His Ala Gln Ala Asp Gly Thr Gly Pro Gly Gly Asn Thr
         195                200                205

AAA ACA GGT CGT TAT GAA TAC GGT TCT GAC TTT CCT CCG TTT GTC ATC              732
Lys Thr Gly Arg Tyr Glu Tyr Gly Ser Asp Phe Pro Pro Phe Val Ile
     210                215                220

GAT AAA GTC GGC ACT AAG TGT TCA ATG AAC AAC AGC GCG GTA AGA ACG              780
Asp Lys Val Gly Thr Lys Cys Ser Met Asn Asn Ser Ala Val Arg Thr
225                230                235                240

GTT GAC CTG AAC GGC TCA ACT TCA GGT AAC ACC ACT TAC AGC TAT ACC              828
Val Asp Leu Asn Gly Ser Thr Ser Gly Asn Thr Thr Tyr Ser Tyr Thr
                 245                250                255
```

FIG. IA

```
TGT AAC GAC TCA ACC AAC TAC AAC GAT TAC AAA GCC ATT AAC GGC GCG      876
Cys Asn Asp Ser Thr Asn Tyr Asn Asp Tyr Lys Ala Ile Asn Gly Ala
            260             265             270

TAC TCG CCA CTG AAC GAT GCC CAC TAC TTC GGT AAA GTG GTT TTC GAT      924
Tyr Ser Pro Leu Asn Asp Ala His Tyr Phe Gly Lys Val Val Phe Asp
        275             280             285

ATG TAC AAA GAC TGG ATG AAC ACC ACA CCA CTG ACG TTC CAG CTG ACT      972
Met Tyr Lys Asp Trp Met Asn Thr Thr Pro Leu Thr Phe Gln Leu Thr
        290             295             300

ATG CGT GTT CAC TAT GGT AAC AAC TAC GAA AAC GCG TTC TGG AAT GGT     1020
Mat Arg Val His Tyr Gly Asn Asn Tyr Glu Asn Ala Phe Trp Asn Gly
305             310             315             320

TCA TCC ATG ACC TTC GGT GAT GGC TAC AGC ACC TTC TAC CCG CTG GTG     1068
Ser Ser Met Thr Phe Gly Asp Gly Tyr Ser Thr Phe Tyr Pro Leu Val
                325             330             335

GAT ATT AAC GTT AGT GCC CAC GAA GTG AGC CAC GGT TTC ACC GAA CAA     1116
Asp Ile Asn Val Ser Ala His Glu Val Ser His Gly Phe Thr Glu Gln
            340             345             350

AAC TCG GGT CTG GTG TAC GAG AAT ATG TCT GGT GGT ATG AAC GAA GCG     1164
Asn Ser Gly Leu Val Tyr Glu Asn Met Ser Gly Gly Met Asn Glu Ala
        355             360             365

TTC TCT GAT ATT GCA GGT GAA GCA GCA GAG TTC TAC ATG AAA GGC AGC     1212
Phe Ser Asp Ile Ala Gly Glu Ala Ala Glu Phe Tyr Met Lys Gly Ser
    370             375             380

GTT GAC TGG GTT GTC GGT GCG GAT ATC TTC AAA TCA TCC GGC GGT CTG     1260
Val Asp Trp Val Val Gly Ala Asp Ile Phe Lys Ser Ser Gly Gly Leu
385             390             395             400

CGT TAC TTT GAT CAG CCT TCG CGT GAC GGC CGT TCT ATC GAC CAT GCG     1308
Arg Tyr Phe Asp Gln Pro Ser Arg Asp Gly Arg Ser Ile Asp His Ala
                405             410             415

TCT GAC TAC TAC AAT GGC CTG AAT GTT CAC TAC TCA AGT GGT GTA TTC     1356
Ser Asp Tyr Tyr Asn Gly Leu Asn Val His Tyr Ser Ser Gly Val Phe
            420             425             430

AAC CGT GCG TTC TAC CTG CTG GCT AAC AAA GCG GGT TGG GAT GTA CGC     1404
Asn Arg Ala Phe Tyr Leu Leu Ala Asn Lys Ala Gly Trp Asp Val Arg
        435             440             445

AAA GGC TTT GAA GTG TTT ACC CTG GCT AAC CAA TTG TAC TGG ACA GCG     1452
Lys Gly Phe Glu Val Phe Thr Leu Ala Asn Gln Leu Tyr Trp Thr Ala
    450             455             460

AAC AGC ACA TTT GAT GAA GGC GGT TGT GGT GTA GTG AAA GCT GCG AGC     1500
Asn Ser Thr Phe Asp Glu Gly Gly Cys Gly Val Val Lys Ala Ala Ser
465             470             475             480

GAC ATG GGT TAC AGC GTT GCA GAC GTA GAA GAT GCG TTT AAC ACG GTA     1548
Asp Met Gly Tyr Ser Val Ala Asp Val Glu Asp Ala Phe Asn Thr Val
                485             490             495

GGC GTT AAC GCG TCT TGT GGT GCA ACT CCT CCT CCG TCT GGC GAT GTA     1596
Gly Val Asn Ala Ser Cys Gly Ala Thr Pro Pro Pro Ser Gly Asp Val
            500             505             510
```

FIG. 1B

```
CTG GAA ATC GGT AAA CCG CTG GCG AAC CTT TCA GGT AAC CGC AAT GAC    1644
Leu Glu Ile Gly Lys Pro Leu Ala Asn Leu Ser Gly Asn Arg Asn Asp
        515                 520                 525

ATG ACT TAC TAC ACG TTC ACA CCA AGC AGC TCA TCT AGC GTA GTG ATT    1692
Met Thr Tyr Tyr Thr Phe Thr Pro Ser Ser Ser Ser Ser Val Val Ile
    530                 535                 540

AAG ATC ACT GGC GGT ACA GGT GAT GCA GAC CTT TAC GTG AAA GCG GGT    1740
Lys Ile Thr Gly Gly Thr Gly Asp Ala Asp Leu Tyr Val Lys Ala Gly
545                 550                 555                 560

AGC AAG CCA ACC ACG ACT TCT TAC GAT TGC CGT CCA TAT AAG TAT GGT    1788
Ser Lys Pro Thr Thr Thr Ser Tyr Asp Cys Arg Pro Tyr Lys Tyr Gly
                565                 570                 575

AAC GAA GAG CAG TGT TCA ATT TCA GCG CAA GCG GGT ACT ACG TAT CAC    1836
Asn Glu Glu Gln Cys Ser Ile Ser Ala Gln Ala Gly Thr Thr Tyr His
            580                 585                 590

GTT ATG CTG CGT GGT TAC AGC AAT TAC GCT GGT GTA ACT TTG CGT GCT    1884
Val Met Leu Arg Gly Tyr Ser Asn Tyr Ala Gly Val Thr Leu Arg Ala
        595                 600                 605

GAC TAA ACTCAGAATG GAACCAGTGA AGGCGCACCT TAAGGTCGCC TTTTTTGTAT    1932
Asp Ter
609

CAGGCGATCT GTGTAAACGT GACCTGATCG AAGTGAGGAT TGGCCGCCAG CGCTTGCATG  1980
```

FIG. IC

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 2000 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO:1:

```
TTTAATTTCT GATTTATCAG TAGTTAAACA ACGATTGAAA ATAATCTCCA GGATTGAGAA            60

ATG AAT AAA ACA CAA CGT CAC ATC AAC TGG CTG CTG GCT GTT AGC GCG            108
Met Asn Lys Thr Gln Arg His Ile Asn Trp Leu Leu Ala Val Ser Ala
1               5                   10                  15

GCA ACT GCG CTA CCT GTC ACC GCT GCA GAA ATG ATC AAC GTA AAT GAT            156
Ala Thr Ala Leu Pro Val Thr Ala Ala Glu Met Ile Asn Val Asn Asp
                20                  25                  30

GGC AGC CTG CTA AAC CAG GCT CTT AAA GCT CAG TCA CAG AGC GTT GCC            204
Gly Ser Leu Leu Asn Gln Ala Leu Lys Ala Gln Ser Gln Ser Val Ala
            35                  40                  45

CCG GTG GAA ACC GGA TTC AAA CAA ATG AAA CGA GTT GTT TTG CCA AAT            252
Pro Val Glu Thr Gly Phe Lys Gln Met Lys Arg Val Val Leu Pro Asn
        50                  55                  60

GGC AAA GTG AAA GTT CGT TAT CAA CAA ACT CAC CAC GGT CTA CCG GTT            300
Gly Lys Val Lys Val Arg Tyr Gln Gln Thr His His Gly Leu Pro Val
65                  70                  75                  80

TTC AAC ACC TCG GTA GTG GCG ACT GAA TCG AAG TCT GGT AGT AGC GAA            348
Phe Asn Thr Ser Val Val Ala Thr Glu Ser Lys Ser Gly Ser Ser Glu
                85                  90                  95

GTG TTC GGT GTG ATG GCT CAG GGT ATC GCA GAC GAC GTG TCT ACA CTG            396
Val Phe Gly Val Met Ala Gln Gly Ile Ala Asp Asp Val Ser Thr Leu
                100                 105                 110

ACG CCA TCC GTT GAG ATG AAG CAG GCC ATT TCA ATT GCT AAA TCG CGT            444
Thr Pro Ser Val Glu Met Lys Gln Ala Ile Ser Ile Ala Lys Ser Arg
            115                 120                 125

TTC CAA CAG CAA GAA AAA ATG GTT GCG GAA CCT GCA ACG GAA AAC GAA            492
Phe Gln Gln Gln Glu Lys Met Val Ala Glu Pro Ala Thr Glu Asn Glu
        130                 135                 140

AAA GCC GAG TTG ATG GTT CGT CTG GAC GAC AAC AAT CAA GCG CAA CTA            540
Lys Ala Glu Leu Met Val Arg Leu Asp Asp Asn Asn Gln Ala Gln Leu
145                 150                 155

GTG TAT CTG GTT GAT TTC TTC GTT GCC GAG GAT CAC CCA GCG CGT CCT            588
Val Tyr Leu Val Asp Phe Phe Val Ala Glu Asp His Pro Ala Arg Pro
                165                 170                 175

TTC TTT TTC ATT GAT GCG CAA ACG GGT GAA GTA CTG CAA ACT TGG GAT            636
Phe Phe Phe Ile Asp Ala Gln Thr Gly Glu Val Leu Gln Thr Trp Asp
                180                 185                 190

GGT CTG AAC CAT GCA CAA GCT GAC GGT ACT GGC CCT GGC GGT AAC ACC            684
Gly Leu Asn His Ala Gln Ala Asp Gly Thr Gly Pro Gly Gly Asn Thr
            195                 200                 205
```

| | | | | | | | | | | | | | | | |
|---|---|---|---|---|---|---|---|---|---|---|---|---|---|---|---|
| AAA | ACA | GGT | CGT | TAT | GAA | TAC | GGT | TCT | GAC | TTT | CCT | CCG | TTT | GTC | ATC | 732 |
| Lys | Thr | Gly | Arg | Tyr | Glu | Tyr | Gly | Ser | Asp | Phe | Pro | Pro | Phe | Val | Ile | |
| | | 210 | | | | 215 | | | | | 220 | | | | | |
| GAT | AAA | GTC | GGC | ACT | AAG | TGT | TCA | ATG | AAC | AAC | AGC | GCG | GTA | AGA | ACG | 780 |
| Asp | Lys | Val | Gly | Thr | Lys | Cys | Ser | Met | Asn | Asn | Ser | Ala | Val | Arg | Thr | |
| 225 | | | | | 230 | | | | | 235 | | | | | | |
| GTT | GAC | CTG | AAC | GGC | TCA | ACT | TCA | GGT | AAC | ACC | ACT | TAC | AGC | TAT | ACC | 828 |
| Val | Asp | Leu | Asn | Gly | Ser | Thr | Ser | Gly | Asn | Thr | Thr | Tyr | Ser | Tyr | Thr | |
| | | | | | 245 | | | | 250 | | | | | 255 | | |
| TGT | AAC | GAC | TCA | ACC | AAC | TAC | AAC | GAT | TAC | AAA | GCC | ATT | AAC | GGC | GCG | 876 |
| Cys | Asn | Asp | Ser | Thr | Asn | Tyr | Asn | Asp | Tyr | Lys | Ala | Ile | Asn | Gly | Ala | |
| | | | 260 | | | | | 265 | | | | | 270 | | | |
| TAC | TCG | CCA | CTG | AAC | GAT | GCC | CAC | TAC | TTC | GGT | AAA | GTG | GTT | TTC | GAT | 924 |
| Tyr | Ser | Pro | Leu | Asn | Asp | Ala | His | Tyr | Phe | Gly | Lys | Val | Val | Phe | Asp | |
| | | 275 | | | | | 280 | | | | | 285 | | | | |
| ATG | TAC | AAA | GAC | TGG | ATG | AAC | ACC | ACA | CCA | CTG | ACG | TTC | CAG | CTG | ACT | 972 |
| Met | Tyr | Lys | Asp | Trp | Met | Asn | Thr | Thr | Pro | Leu | Thr | Phe | Gln | Leu | Thr | |
| | 290 | | | | | 295 | | | | | 300 | | | | | |
| ATG | CGT | GTT | CAC | TAT | GGT | AAC | AAC | TAC | GAA | AAC | GCG | TTC | TGG | AAT | GGT | 1020 |
| Met | Arg | Val | His | Tyr | Gly | Asn | Asn | Tyr | Glu | Asn | Ala | Phe | Trp | Asn | Gly | |
| 305 | | | | | 310 | | | | | 315 | | | | | | |
| TCA | TCC | ATG | ACC | TTC | GGT | GAT | GGC | TAC | AGC | ACC | TTC | TAC | CCG | CTG | GTG | 1068 |
| Ser | Ser | Met | Thr | Phe | Gly | Asp | Gly | Tyr | Ser | Thr | Phe | Tyr | Pro | Leu | Val | |
| | | | | 325 | | | | | 330 | | | | | 335 | | |
| GAT | ATT | AAC | GTT | AGT | GCC | CAC | GAA | GTG | AGC | CAC | GGT | TTC | ACC | GAA | CAA | 1116 |
| Asp | Ile | Asn | Val | Ser | Ala | His | Glu | Val | Ser | His | Gly | Phe | Thr | Glu | Gln | |
| | | | 340 | | | | | 345 | | | | | 350 | | | |
| AAC | TCG | GGT | CTG | GTG | TAC | GAG | AAT | ATG | TCT | GGT | GGT | ATG | AAC | GAA | GCG | 1164 |
| Asn | Ser | Gly | Leu | Val | Tyr | Glu | Asn | Met | Ser | Gly | Gly | Met | Asn | Glu | Ala | |
| | | 355 | | | | | 360 | | | | | 365 | | | | |
| TTC | TCT | GAT | ATT | GCA | GGT | GAA | GCA | GCA | GAG | TTC | TAC | ATG | AAA | GGC | AGC | 1212 |
| Phe | Ser | Asp | Ile | Ala | Gly | Glu | Ala | Ala | Glu | Phe | Tyr | Met | Lys | Gly | Ser | |
| | 370 | | | | | 375 | | | | | 380 | | | | | |
| GTT | GAC | TGG | GTT | GTC | GGT | GCG | GAT | ATC | TTC | AAA | TCA | TCC | GGC | GGT | CTG | 1260 |
| Val | Asp | Trp | Val | Val | Gly | Ala | Asp | Ile | Phe | Lys | Ser | Ser | Gly | Gly | Leu | |
| 385 | | | | | 390 | | | | | 395 | | | | | | |
| CGT | TAC | TTT | GAT | CAG | CCT | TCG | CGT | GAC | GGC | CGT | TCT | ATC | GAC | CAT | GCG | 1308 |
| Arg | Tyr | Phe | Asp | Gln | Pro | Ser | Arg | Asp | Gly | Arg | Ser | Ile | Asp | His | Ala | |
| | | | | 405 | | | | | 410 | | | | | 415 | | |
| TCT | GAC | TAC | TAC | AAT | GGC | CTG | AAT | GTT | CAC | TAC | TCA | AGT | GGT | GTA | TTC | 1356 |
| Ser | Asp | Tyr | Tyr | Asn | Gly | Leu | Asn | Val | His | Tyr | Ser | Ser | Gly | Val | Phe | |
| | | | 420 | | | | | 425 | | | | | 430 | | | |
| AAC | CGT | GCG | TTC | TAC | CTG | CTG | GCT | AAC | AAA | GCG | GGT | TGG | GAT | GTA | CGC | 1404 |
| Asn | Arg | Ala | Phe | Tyr | Leu | Leu | Ala | Asn | Lys | Ala | Gly | Trp | Asp | Val | Arg | |
| | | 435 | | | | | 440 | | | | | 445 | | | | |
| AAA | GGC | TTT | GAA | GTG | TTT | ACC | CTG | GCT | AAC | CAA | TTG | TAC | TGG | ACA | GCG | 1452 |
| Lys | Gly | Phe | Glu | Val | Phe | Thr | Leu | Ala | Asn | Gln | Leu | Tyr | Trp | Thr | Ala | |
| | 450 | | | | | 455 | | | | | 460 | | | | | |
| AAC | AGC | ACA | TTT | GAT | GAA | GGC | GGT | TGT | GGT | GTA | GTG | AAA | GCT | GCG | AGC | 1500 |
| Asn | Ser | Thr | Phe | Asp | Glu | Gly | Gly | Cys | Gly | Val | Val | Lys | Ala | Ala | Ser | |
| 465 | | | | | 470 | | | | | 475 | | | | | | |
| GAC | ATG | GGT | TAC | AGC | GTT | GCA | GAC | GTA | GAA | GAT | GCG | TTT | AAC | ACG | GTA | 1548 |
| Asp | Met | Gly | Tyr | Ser | Val | Ala | Asp | Val | Glu | Asp | Ala | Phe | Asn | Thr | Val | |
| | | | | 485 | | | | | 490 | | | | | 495 | | |
| GGC | GTT | AAC | GCG | TCT | TGT | GGT | GCA | ACT | CCT | CCT | CCG | TCT | GGC | GAT | GTA | 1596 |
| Gly | Val | Asn | Ala | Ser | Cys | Gly | Ala | Thr | Pro | Pro | Pro | Ser | Gly | Asp | Val | |
| | | | | 500 | | | | | 505 | | | | | 510 | | |
| CTG | GAA | ATC | GGT | AAA | CCG | CTG | GCG | AAC | CTT | TCA | GGT | AAC | CGC | AAT | GAC | 1644 |
| Leu | Glu | Ile | Gly | Lys | Pro | Leu | Ala | Asn | Leu | Ser | Gly | Asn | Arg | Asn | Asp | |
| | | 515 | | | | | 520 | | | | | 525 | | | | |

| | | | | | | | | | | | | | | | | |
|---|---|---|---|---|---|---|---|---|---|---|---|---|---|---|---|---|
| ATG | ACT | TAC | TAC | ACG | TTC | ACA | CCA | AGC | AGC | TCA | TCT | AGC | GTA | GTG | ATT | 1692 |
| Met | Thr | Tyr | Tyr | Thr | Phe | Thr | Pro | Ser | Ser | Ser | Ser | Ser | Val | Val | Ile | |
| | 530 | | | | | 535 | | | | | 540 | | | | | |
| AAG | ATC | ACT | GGC | GGT | ACA | GGT | GAT | GCA | GAC | CTT | TAC | GTG | AAA | GCG | GGT | 1740 |
| Lys | Ile | Thr | Gly | Gly | Thr | Gly | Asp | Ala | Asp | Leu | Tyr | Val | Lys | Ala | Gly | |
| 545 | | | | | 550 | | | | | 555 | | | | | | |
| AGC | AAG | CCA | ACC | ACG | ACT | TCT | TAC | GAT | TGC | CGT | CCA | TAT | AAG | TAT | GGT | 1788 |
| Ser | Lys | Pro | Thr | Thr | Thr | Ser | Tyr | Asp | Cys | Arg | Pro | Tyr | Lys | Tyr | Gly | |
| | | | | 565 | | | | | 570 | | | | | 575 | | |
| AAC | GAA | GAG | CAG | TGT | TCA | ATT | TCA | GCG | CAA | GCG | GGT | ACT | ACG | TAT | CAC | 1836 |
| Asn | Glu | Glu | Gln | Cys | Ser | Ile | Ser | Ala | Gln | Ala | Gly | Thr | Thr | Tyr | His | |
| | | 580 | | | | | | 585 | | | | | 590 | | | |
| GTT | ATG | CTG | CGT | GGT | TAC | AGC | AAT | TAC | GCT | GGT | GTA | ACT | TTG | CGT | GCT | 1884 |
| Val | Met | Leu | Arg | Gly | Tyr | Ser | Asn | Tyr | Ala | Gly | Val | Thr | Leu | Arg | Ala | |
| | | 595 | | | | | 600 | | | | | 605 | | | | |
| GAC | TAA | ACTCAGAATG | GAACCAGTGA | AGGCGCACCT | TAAGGTCGCC | TTTTTTGTAT | | | | | | | | | | 1940 |
| Asp | Ter | | | | | | | | | | | | | | | |
| 609 | | | | | | | | | | | | | | | | |
| CAGGCGATCT | GTGTAAACGT | GACCTGATCG | AAGTGAGGAT | TGGCCGCCAG | CGCTTGCATG | | | | | | | | | | | 2000 |

COMPOSITIONS CONTAINING PROTEASE PRODUCED BY VIBRIO AND METHOD OF USE IN DEBRIDEMENT AND WOUND HEALING

This application is a continuation of application Ser. No. 08/086,465, filed Jul. 6, 1993, now abandoned, in turn a continuation of application Ser. No. 07/670,612, filed on Mar. 13, 1991, now abandoned, in turn a CIP of application Ser. No. 07/567,884, filed on Aug. 15, 1990, now U.S. Pat. No. 5,145,681.

TECHNICAL FIELD

The present invention relates to debriding compositions and to methods using such compositions for debridement and/or wound healing, which contain certain proteases produced by microorganisms of the genus Vibrio. More particularly, the protease is capable of effectively digesting necrotic tissue while viable living tissue is not substantially injured. The protease also has wound healing properties.

BACKGROUND OF THE INVENTION

The healing of wounds is a complex process which is often further complicated by the presence of non-viable, necrotic tissue in the wound area. Debridement is the process of removing the non-viable tissue from a wound to prevent infection and facilitate healing.

Considerable efforts have been made to discover materials capable of distinguishing between viable and non-viable tissue. The discovery of materials which would digest devitalized tissue while not attacking viable tissue would make it possible to remove the devitalized tissue without surgery. It would be a beneficial therapeutic agent in virtually all disease processes where topically devitalized tissue needs to be removed from the viable organism such as burns, decubitus ulcers, pressure necroses, incisional, traumatic and pyogenic wounds, and ulcers secondary to peripheral vascular disease.

One area that has attracted considerable attention is the use of proteolytic enzymes and other chemicals to effect the early debridement of eschar tissue, resulting from burns. Such devitalized tissue is an excellent culture medium and the principal source of the septicemia which is the proximate cause of death in the majority of severely burned patients.

In burns, the devitalized tissue is referred to as eschar. Burn eschar is a complex mixture of dried blood, purulent exudates, and denatured proteins normally found in the epidermal and dermal skin layers. The denatured proteins found in eschar are primarily collagen, elastin, fibrin, hemoglobin, and other coagulated proteins.

Collagen comprises about 75% of the skin's dry weight and is the main constituent of the necrotic debris and of eschar. Strands of semi-viable, compromised collagen, whose protective mucopolysaccharide sheath has been damaged or destroyed, anchor the necrotic tissue to the wound surface. These strands, which appear as a layer of whitish, persistent microscopic fibrils, have been termed 'collagen moss'; they must be fully eliminated in order for the necrotic material to be separated from its base. This complete debridement then permits development of granulation tissue.

For a proteolytic enzyme to be most useful as a debriding agent, particularly for burns, it is desirable for the protease to distinguish between viable and non-viable tissue; readily and thoroughly hydrolyze a wide variety of denatured proteins found in eschar; function at physiological pH and temperature; be compatible with adjunct therapies (e.g., cleansing agents, topical antibiotics); not interfere with normal wound healing or complicate skin grafting; and remain stable in various formulations and at a wide range of temperatures. A number of proteolytic enzyme preparations have been used as debriding agents with varying degrees of success.

Travase® ointment, which is a preparation containing proteolytic enzymes obtained from sterile filtrates of *Bacillus subtilis*, is another known enzymatic debriding agent (Garrett, *Clinical Medicine* (1969) 76:11–15) and U.S. Pat. No. 3,409,719. Crikelair (U.S. Pat. No. 4,276,281) describes the use of elastase, a serine protease derived from pancreas, as an enzymatic debridement agent. Klein et al. (U.S. Pat. No. 4,329,430) describe a proteolytic enzyme mixture derived from bromelin which is useful for the digestion, dissection and separation of non-viable, devitalized tissue. Schmitt (U.S. Pat. No. 3,983,209) teaches treating burns in animals by applying enzymes to a burn surface for debridement of eschar and necrotic tissue. The enzymes disclosed included papain, trypsin, lysozyme, streptokinase, fibrinolysin, pinguinain, Travase and bromelain in a specified hydrophobic polymer. Bioerosion over prolonged periods of time slowly released the proteolytic enzymes.

Merkel (U.S. Pat. No. 3,677,900) discloses that collagenases, especially those produced by a species of Vibrio, are useful as debriding agents. However, Merkel's collagenase is an enzyme capable of digesting native, undenatured collagen under physiological conditions of pH and temperature and is not inhibited by serum. The Merkel collagenase therefore is not likely to distinguish between viable and non-viable tissue. Collagenases also have a very narrow substrate specificity. Further, collagenase has been reported to cause significant damage to viable dermal tissue, causing reduced granulation tissue development and wound maturation (Hamit et al., Ann. Surg. (1960) 151:589).

Further, proteolytic enzymes have been speculated to be useful in prevention of surgical adhesions (Ellis, *Br. J. Surg.* (1982) 69:241–243). Adhesions are characterized by fibrinous formations which develop within a few hours of operational trauma and become organized by the ingrowth of fibroblasts and blood capillaries to form established fibrous adhesions. Intra-abdominal adhesions are almost inevitable after major abdominal surgery. These adhesions make reoperation on the abdomen a tedious dissection, with risk of visceral damage, and they may precipitate intestinal obstruction. Numerous protein preparations have been tried, with varying degrees of success, to prevent surgical adhesions including heparin, corticosteroids, antihistamines, plasmin, streptokinase, dextran, and tissue plasminogen activator (Doody et al., *Fertil and Steril* (1989) 51:509–512), and no agent has proven to be consistently effective.

While other proteolytic agents are known which have speculated debriding and anti-adhesion properties, many of these agents have been shown to be ineffective and cause local or systemic toxicity. None of the previous proteolytic agents have the superior characteristics of the present invention, including debridement properties and the ability to promote the wound healing process.

SUMMARY OF THE INVENTION

This invention provides compositions for treating wounds comprising a pharmaceutically acceptable topical carrier admixed with an effective amount of a protease selected from the group consisting of
- (a) an extracellular neutral protease produced by cultivation of a microorganism belonging to the genus Vibrio characterized by the following properties:
  - i. hydrolyzes components of necrotic tissue including denatured collagen, elastin and fibrin;
  - ii. does not substantially hydrolyze native tissue in vivo; and
  - iii. exhibits stable activity when stored at 25° C. in a topical formulation.
- (b) a protease expressed by recombinant host cells which have been transformed or transfected with an expression vector for said protease (a); and
- (c) mutants and hybrids of proteases (a) and (b) which are characterized by the properties (i) to (ii).

Also provided are methods of debriding wounds which comprise contacting a wound with an effective amount of such Vibrio protease-containing compositions.

It is a primary object of this invention to provide compositions and methods of debriding wounds wherein the active ingredient is a protease isolated from the Vibrio strain *Vibrio proteolyticus* ATCC 53559. Further, said protease has a DNA sequence as illustrated in FIG. 1 (SEQ ID NO. 1).

It is a further object to provide compositions for debriding wounds wherein the pharmaceutically acceptable topical carrier is either hydrophobic or hydrophilic. Hydrophilic formulations are particularly preferred. The compositions demonstrate substantial enzyme stability when stored at 25° C. The enzyme exhibits about 80% to about 95% activity when stored at 25° C. in a topical formulation.

Another object is the ability of the compositions and methods of the invention to have debriding effects on a wide variety of wounds including, but not limited to, management of full and partial thickness burn wounds; debridement of ulcerative lesions, principally pressure (decubitus) ulcers and varicose, stasis and trophic ulcers; preparation of skin graft sites and general surgical wounds such as amputation, incisional, traumatic and pyogenic wounds; treatment of vaginitis, cervicitis, circumcisions, episitomy, pilonidal cyst wounds, carbuncles, sunburn, frostbite, and cataract scar tissue.

A further object of the invention is to provide compositions and methods which have wound healing properties. Wound healing properties include ability to increase the rate at which wounds heal and also the ability to improve wound healing (i.e., maintain response to tactile stimulus, less scarring, improved neovascularization, etc.). The wound healing properties include the prevention of adhesions caused by surgical or other wounds. Wound healing can be divided into four essential components: inflammation, angiogenesis, collagen deposition and epithelialization. All of these play a role in the healing of all wounds. Particularly, the compositions of the invention exhibit the ability to cause wound contracture.

BRIEF DESCRIPTION OF THE DRAWINGS

FIG. 1 (3 pages) is a representation of the DNA sequence of the vibriolysin gene (SEQ ID NO. 1). The DNA sequence illustrated comprises a portion of a 6.7 kb Hind III fragment of the *Vibrio proteolyticus* gene (described in U.S. Pat. No. 4,966,846 which encodes vibriolysin). An open reading frame exists from approximately base 249–2078, within which the DNA region encoding vibriolysin is found.

DETAILED DESCRIPTION OF THE INVENTION

Figure 2:
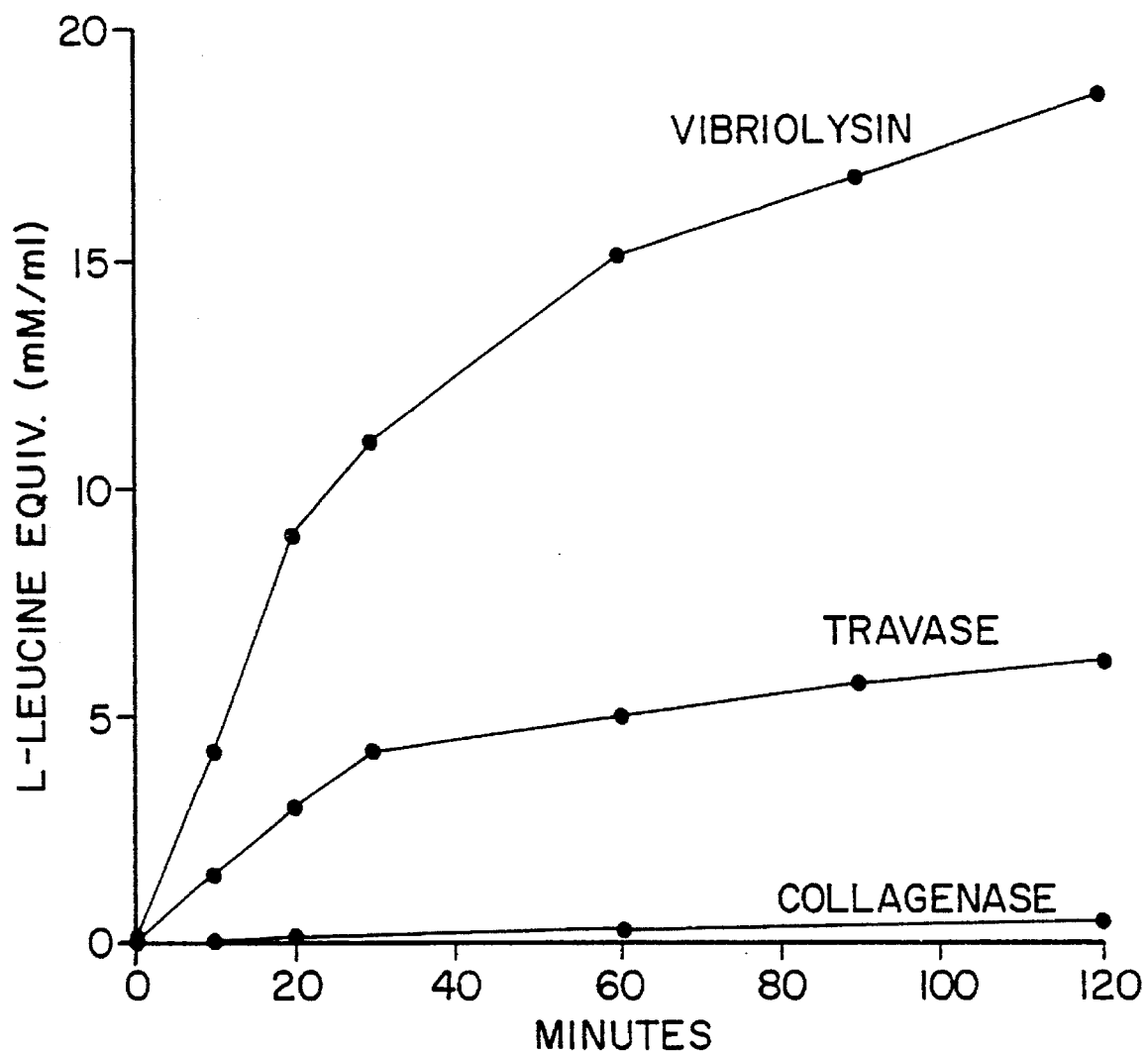
FIG. 2 compares the ability of vibriolysin, Travase, and collagenase to act on the substrate fibrin.

The proteases of this invention are characterized by a combination of properties which renders them ideal candidates for use in wound debridement and healing applications. By way of illustration and not limitation, such properties include:
- i. hydrolyzes components of necrotic tissue including denatured collagen, elastin and fibrin;
- ii. does not substantially hydrolyze native tissue in vivo; and
- iii. exhibits stable activity when stored at 25° C. in a topical formulation.

The proteases of the invention are capable of distinguishing between viable and non-viable, necrotic tissue and are also active for sustained periods in formulations which are unacceptable to other proteases.

For the purposes of this application and the appended claims, the aforementioned properties of the proteases of this invention are determined as follows: For initial in vitro efficacy studies with the proteases of this invention, constituent proteins associated with eschar (e.g., denatured collagen, fibrin, denatured elastin) and native tissue were subjected to enzymatic hydrolysis. For comparison, the proteases (sutilains) derived from *Bacillus subtilis* were used. These proteases are formulated into a hydrophobic base and distributed commercially as Travase™ ointment (Boots-Flint Laboratories, Morton Grove, Ill.). The proteases from Travase ointment were extracted as described in official monographs of the United States Pharmacopoeia XXII (1990; p. 1306) and will henceforth be referred to as Travase proteases. For assessment of hydrolysis of each substrate, vibriolysin and Travase proteases were added to each reaction mixture to an equivalent activity unit basis as determined by the azocasein assay described below.

A. Azocasein Hydrolysis

Azocasein is a readily available protein that is used as a standard for measuring protease activity. A sample of protease is incubated for ten minutes at 37° C. in 50 mM Tris-HCl buffer (pH 7.4) containing 1.0 mg/ml of azocasein (sulfanilamideazocasein, Sigma Corp., St. Louis, Mo.) with a final volume of 0.5 ml. At the end of this incubation period, 0.5 ml of 10% w/v trichloroacetic acid are added and immediately mixed and the resulting mixture is then stored on ice for 10 minutes. The mixture is then centrifuged and the optical density of the resulting supernatant is determined at 420 nm against a blank that contains either no enzyme or inactivated enzyme in the buffered azocasein solution. One unit of activity is defined as the amount of enzyme required to cause a change in absorbance of 2.5 at 420 nm.

B. Ninhydrin Assay

Nonspecific hydrolysis of various substrates resulting in the release of peptides and free amino acids was measured by the ninhydrin method (Moore and Stein. *J. Biol. Chem.* (1948) 176:367) as described by a modification of the procedure of Mandl et al. (*J. Clin. Invest.* (1953) 32:1323). Fifty to one hundred microliters of clarified hydrolysis sample were added to a 1.0 ml mixture containing 0.5 ml of 4% ninhydrin in methylcellusolve and 0.5 ml of 0.2M citric acid (pH 5.0 containing 7.1 mM stannous chloride). The solution was boiled for 20 minutes, then chilled in an ice bath. Fifty microliters were added to 1.0 ml 50% n-propanol and the absorbance of the solution was read in a Shimadzu Spectrophotometer at 600 nm against a water blank. Leucine was used as a reference standard.

Clinical Properties of the Protease

The proteases of this invention are well suited for use in treating wounds and are particularly useful in wound debridement and wound healing applications. The properties can be demonstrated in a number of test situations, including animal and human clinical trials. The most widely used assay is a partial thickness burn wound on pigs described by Mertz et al. (Journal Surgical Research (1990) 48:245–248). In this assay, the formulated protease can be compared to various controls to determine effectiveness.

For wound debridement, effectiveness is determined, among other indications, by absence, softening or dissolving of eschar; non-hydrolysis of viable tissue components; and/ or non-irritation of the wound. For topical wound healing, effectiveness is determined, among other indication by wound contracture, increased rate of healing and/or improved healing (i.e., maintain response to tactile stimulus, less scarring, improved neovascularization, etc.).

The wound healing properties of the proteases of the invention are not limited to topical applications only. The wound healing properties can include the prevention and possibly the treatment of adhesions caused by surgical or other wounds.

As mentioned earlier, adhesions are bundles of fibrin and collagen which develop initially as fibrinous formations, usually in the abdomen, after operational or other trauma. Although most adhesions do not result in clinical morbidity, their role as a cause of small bowel obstruction and infertility is well recognized.

In experimental models, adhesions may be induced by thermal or mechanical trauma, ischemia, inflammation or foreign materials. A well known model for determining the effectiveness of the protease of the invention in the reduction of adhesion formation is a rabbit uterine horn model (Doody et al., *Fertil & Steril* (1989) 51:509–512). Effectiveness is determined in this model by reduced adhesion quantity and/or reduced adhesion density as compared to controls.

Preparation of the Protease

The proteases of this invention are produced by fermentation of a suitable Vibrio species in a nutrient medium and then recovering the protease from the resulting broth. Fermentation is conducted aerobically in, for example, a casein hydrolysate, NZ-amine B, or soy flour nutrient medium containing inorganic salts such as sea salts, sodium sulfate, potassium dihydrogen phosphate, magnesium sulfate and certain trace elements at a pH of from about 7.6 to 8.6, preferably about pH 7.8, and at a temperature of from about 25° to 30° C., e.g., about 27° C., until the culture reaches early stationary phase growth.

The enzyme may thereafter be recovered from the fermentation broth by conventional procedures. Typically, the broth is first centrifuged or filtered to separate the cell portion and insoluble material. Thereafter, the supernatant is concentrated by, e.g., ultrafiltration. The resulting ultrafiltrate may be used as is or may be precipitated with organic solvents such as acetone or inorganic salts such as ammonium sulfate, followed by centrifugation, ion-exchange chromatography or filtration in order to isolate an enzyme useful in debriding compositions. The protease is also stable when lyophilized. Other procedures such as are routine to those skilled in the art may also be used to cultivate the Vibrio microorganism and to recover the protease of this invention therefrom.

Useful microorganisms for use as a source of the instant proteases may comprise any suitable Vibrio, Aeromonas, Pseudomonas, Serratia or Bacillus or other marine microorganism species which secretes a protease having the above properties. A particularly preferred microorganism for this purpose is *Vibrio proteolyticus* (ATCC 53559). A viable culture of this microorganism has been irrevocably deposited with the American Type Culture Collection (ATCC), 12301 Parklawn Drive, Rockville, Md. 20852, with no restrictions as to availability, and W. R. Grace & Co.-Conn., the assignee hereof, assures permanent availability of the culture to the public through ATCC upon the grant hereof. The DNA sequence of the protease secreted by *Vibrio proteolyticus* (ATCC 53559), referred to herein as vibriolysin, is set forth in FIG. 1. While *Vibrio proteolyticus* (ATCC 53559) comprises the preferred protease source, other species of useful Vibrio microorganisms can readily be identified by those skilled in the art by screening the proteases produced thereby using the procedures set forth above.

In addition to the direct cultivation of a Vibrio species, the proteases of this invention may also be prepared by the cultivation of recombinant host cells which have been transformed or transfected with a suitable expression vector with an insert containing the structural gene for the Vibrio-derived proteases of this invention. Such procedures may be desirable, for example, in order to increase protease yields over that obtained with the wild type Vibrio microorganism or in order to produce improved mutant proteases.

Techniques for the cloning of proteases are well known to those skilled in the art of recombinant DNA technology, and any suitable cloning procedure may be employed for the preparation of the proteases of this invention. Such procedures are described, for example, in U.S. Pat. No. 4,468,464; European Published Patent Application No. 0 130,756; PCT Published Patent Application No. WO 87/04461; and Loffler, Food Technology, pages 64–70 (January 1986); the entirety of which are hereby incorporated by reference and relied on in their entirety.

A particularly preferred procedure for cloning the Vibrio proteases of this invention is described in commonly assigned U.S. Pat. No. 4,966,846, the entirety of which is hereby incorporated by reference and relied on in its entirety. According to the procedure of this patent, a gene library is first prepared, using the DNA of Vibrio source cells which have been determined by the assays described above to synthesize the proteases of this invention. Chromosomal DNA is extracted from the Vibrio source cells and digested with restriction enzymes by known procedures to give cleavage of the DNA into large fragments. Partial digestion with Sau3A is preferred, although other restriction enzymes (e.g., MboI, BamHI, etc.) may be used. The DNA fragments are then ligated into vectors suitable for allowing isolation of clones which express the protease enzyme. A preferred vector for this purpose is BamHI digested *E. coli* cosmid vector pHC79 (Bethesda Research Laboratories). The recombinant vectors (i.e., pHC79 cosmids containing DNA fragments from the protease-containing genome) are then packaged into bacteriophage particles, preferably bacteriophage lambda, thereby producing a gene library in bacteriophage lambda particles. For production of a gene library in bacteriophage, a cosmid vector or lambda vector is used. In other cases, plasmid vectors may be used.

The resultant bacteriophage particles are then used to insert the gene library DNA fragments into suitable gram-negative host cells. Preferably, the recombinant bacteriophage particles are used to transect *E. coli*, such as, for example, *E. coli* strain HB101, although other strains of *E. coli* may be used if desired. Since *E. coli* strains do not naturally synthesize an extracellar neutral protease enzyme, the *E. coli* clones easily may be evaluated for the presence and expression of the protease gene by the assays described below.

It is known that colonies of Vibrio which synthesize protease enzyme will produce a zone of clearing on milk agar plates due to the proteolytic hydrolysis of the casein component of milk. Non-recombinant *E. coli* colonies do not secrete a protease naturally. Thus, *E. coli* clones of this invention which contain the protease gene are therefore readily identified by this assay. This milk-clearing assay is preferred for use with *E. coli* and other host strains which do not naturally produce an extracellular protease. Other gram-negative and gram-positive strains may be used as hosts.

Confirmation may be made by using other protease assays. For example, clones may be confirmed for expression of the protease enzyme by demonstrating that the fermentation broths of these clones are capable of hydrolyzing substrates such as Hide powder azure, azocoll or N-[3-(2-furyl)acryloyl]-alanyl-phenylalaniamide (FAAPA). Alternatively, these assays may be used in the first instance to identify the protease gene-containing clones.

It is significant in two respects that expression of the neutral protease gene in *E. coli* and other "non-secreting" hosts (that is, hosts which do not naturally secrete a protease) can be detected as a zone of clearing on a milk agar plate. First, this is evidence that the active, functional enzyme is being synthesized by the gram-negative host. Second, the extracellular presence of protease on the milk agar plates is evidence that the enzyme is being externalized in some manner, either by secretion or by cell lysis. Since *E. coli* and some other gram-negative bacteria normally do not secrete significant quantities of proteases into the media, this is important in terms of the ability to recover protease enzymes produced as a result of expression of *Vibrio protease* genes in these non-secreting hosts.

Also contemplated for use herein are mutants and hybrids of the foregoing proteases which substantially retain the preferred performance characteristics. As used herein, the term "mutant" refers to a protease in which a change is present in the amino acid sequence as compared with wild type or parent enzymes. "Hybrid" refers to genetically engineered proteases which combine amino acid sequences from two or more parent enzymes and exhibit characteristics common to both.

Techniques for the preparation of mutant proteases are well known to those skilled in the art and include exposure of a microorganism to radiation or chemicals and site-directed mutagenesis. Mutagenesis by radiation or chemicals is essentially a random process and can require a tedious selection and screening to identify microorganisms which produce enzymes having the desired characteristics. Preferred mutant enzymes for the purposes of this invention are thus prepared by site directed mutagenesis. This procedure involves modification of the enzyme gene such that substitutions, deletions, and/or insertions of at least one amino acid at a predetermined site are produced in the protease enzyme. Techniques for site directed mutagenesis are well known to those skilled in the art and are described, for example, in European Published Patent Application No. 0 130,756 and PCT Published Patent Application No. WO87/04461, the entirety of which are hereby incorporated by reference and relied on in their entirety.

In one such procedure, known as cassette mutagenesis, silent restriction sites are introduced into the protease gene, closely flanking the target codon or codons. Duplex synthetic oligonucleotide cassettes are then ligated into the gap between the restriction sites. The cassettes are engineered to restore the coding sequence in the gap and to introduce an altered codon at the target codon.

The use of such procedures on the parent *Vibrio proteases* may be desirable in order to improve the properties of the wild type or parent protease. For example, the methionine, histidine, cysteine or tryptophan residues in or around the active site of the protease may be replaced in order to improve stability to chemical oxidation, as suggested in Estell et al., *J. Biological Chemistry*, Vol. 260, No. 11, pages 2518–2521 (1985).

Hybrids of the parent or wild type proteases may likewise be prepared by known protein engineering procedures analogous to the above-discussed cassette mutagenesis procedure by ligating a region of the gene of one parent enzyme (which need not be derived from Vibrio) into the gene of a second parent enzyme.

Formulation and Administration

Formulations of the debriding protease using available excipients and carriers are prepared according to standard methods known to those in the art. The protease can be formulated in ointments, lotions, gels, pastes, foams, aerosols, or immobilized on beads. The protease can also be immobilized in a wound dressing, tape or gauze. The enzyme formulations can be either hydrophilic or hydrophobic. Examples of hydrophobic bases include parafin-mineral oil, and hydrophilic bases include petrolatum-propylene water bases. Hydrophilic formulations are preferred, particularly if the enzyme is stable in the formulation during storage at room temperature. Reasons for the preference include not having to raise the temperature of the preparation before administering to the wound. More importantly, enzymes in a hydrophilic ointment should be more accessible for hydrolysis of necrotic tissue, and in contrast to a hydrophobic base, the ointment can be easily removed from the wound by washing with saline. Additional active ingredients, including antibiotics, humectants, deoxyribonucleases, fibronectin, growth factors such as fibroblast growth factor (FGF), epidermal growth factor (EGF), the transforming growth factors (TGF), insulin-like growth factors (IGF-1 and IGF-2), and/or platelet-derived growth factor (PDGF) and the like, can be included in the formulation, if desired.

Topical administration is most appropriate for wound debridement, although other routes of administration may be desirable under certain conditions. Standard topical formulations are employed using, for example, 0.01–10% protease by weight. Such formulations are applied 1–6 times per day to the affected area. The application and concentration of the ointment or other formulation depends, of course, on the severity and type of the wound and nature of the subject.

Topical administration is also appropriate in order to stimulate vascularization and healing of traumatized tissue. Substrates include burns, bone fractures, surgical abrasions such as those of plastic surgery, cuts, lacerations, bed sores, slow-healing ulcers, tendonitis, bursitis, vaginitis, cervicitis, circumcisions, episitomy, pilonidal cyst wounds, carbuncles, sunburn, frostbite. Local, or possibly systemic, administration is appropriate for the prevention, or possibly treatment, of adhesions caused by surgical or other wounds. Local administration can be by injection, subcutaneous implant or slow release formulation implanted directly proximal the target. Implantation is directly practical especially under surgical conditions. Slow-release forms can be formulated in polymers as is well within the skill of the art. The concentration of protease in the formulation depends on a number of factors, including the severity of the condition and the rate of protease release from the polymer. The following abbreviations have been used throughout in describing the invention:

| | |
|---|---|
| $HBO_3$ | boric acid |
| $CaCl_2$ | calcium chloride |
| $CaSO_4$ | calcium sulfate |
| cm | centimeter |
| $CuSO_4$ | copper sulfate |
| °C. | degrees Centigrade |
| g | gram(s) |
| I.M. | intramuscular |
| kb | kilobase pair |
| $MgSO_4$ | magnesium sulfate |
| $MnCl_2$ | manganese chloride |
| mg | milligram(s) |
| ml | milliliter(s) |
| mm | millimeter(s) |
| mM | millimolar |
| M | molar |
| mS | milli semen |
| nm | nanometer(s) |
| O.D. | optical density |
| % | percent |
| $K_2HPO_4$ | potassium phosphate |
| NaOH | sodium hydroxide |
| $Na_2MoO_3$ | sodium molybdate |
| $Na_2SO_4$ | sodium sulfate |
| $H_2O$ | water |
| w/v | weight to volume |
| $ZnSO_4$ | zinc sulfate |

EXAMPLES

The following examples serve to give specific illustration of the practice of this invention, but they are not intended in any way to act to limit the scope of the invention.

EXAMPLE 1

Preparation of Vibriolysin

*V. proteolyticus* ATCC 53559 was cultured in a medium with the following composition (g or ml per liter): NZ-amine B, 40; $Na_2SO_4$, 25; dextrose, 10; $K_2HPO_4$, 4; $MgSO_4$ $7H_2O$, 0.4; Darastil-8270 (Dearborn), 0.1 ml and 6.1 ml of trace elements solution. The trace element solution comprises (grams per liter) the following: $ZnSO_4$ $7H_2O$, 18.29; $MnCl_2$ $4H_2O$, 18.86; $CaSO_4$ $2H_2O$, 0.91 g, $HBO_3$, 0.07; and $Na_2MoO_4$ $2H2O$, 0.04. Prior to sterilization, pH was adjusted to 7.0.

*V. proteolyticus* was cultured in either 1.5- or 10-liter fermentors. Fermentors containing the aforementioned medium were inoculated with 1% (v/v) culture obtained by growing *V. proteolyticus* in shake flasks containing medium of the same composition for 20 hours. The fermentations were performed at 28° C., 1,000–1,250 rpm and an aeration of 1.0 volume of air per volume of medium per minute. The pH of the fermentation was maintained at pH 7.8 by the automatic addition of an acid and base titrant.

Growth of *V. proteolyticus* was monitored by measuring optical density at 640 nm, and protease activity was monitored by the azocasein assay described earlier. During the early stationary growth phase of the fermentation the product protease reaches titers of approximately 85,200 to 127,800 azocasein units/liter as measured by the azocasein assay described earlier. The broth was harvested by centrifugation to separate the cell portion.

The supernatant containing the proteolytic activity was concentrated using an Amicon SlOY10 spiral wound filter (Amicon Corp., Lexington, Mass.). The concentrate was diafiltered with 10 mM Tris buffer containing 1 mM $CaCl_2$ until the conductivity of the rententate was approximately 1 mS and the pH was neutral. This material was lyophilized and stored at −20° C. until use or formulated into an ointment.

EXAMPLE 2

Fibrin Hydrolysis

Fibrin is a protein component found in wound eschar and is found in adhesion development. To measure fibrinolytic activity, human plasma fibrin (Sigma) was hydrolyzed at 37° C. in a reaction vessel containing 10.0 mg fibrin per ml of 100 mM TES (N-tris[hydroxymethyl]methyl-2-aminoethanesulfonic acid) buffer (pH 7.5) containing 0.9% NaCl and 0.1 mM $CaCl_2$. The test enzymes, vibriolysin and Travase, were added to reaction solutions to a concentration of 10 units/ml (azocasein units) with constant mixing; collagenase (0.14 mg/ml, Sigma; Type VII) was added to the reaction. Samples were removed periodically and assayed for free amino groups using the ninhydrin assay described earlier.

The rate of hydrolysis of human fibrin by vibriolysin was approximately four-fold faster than the rate observed with Travase proteases (FIG. 2). Further, the hydrolysis of fibrin was more extensive. In one hour, vibriolysin hydrolyzed 26% of the fibrin substrate as compared to 7.5% for the Travase proteases. These data are highly significant since others have reported that Travase is most effective hydrolyzing fibrin compared to other eschar component [Shakespeare, P.G. et al., *Burns* (1979), 6:15–20] Collagenase, as expected, exhibited no hydrolysis of fibrin (FIG. 2).

EXAMPLE 3

Denatured Collagen Hydrolysis

Eschar associated with deep dermal burns or ulcers has been shown to consist primarily of denatured collagen bound to viable tissue. Thus, an effective debridement agent must digest the collagen component of necrotic tissue. To assess collagen hydrolysis two sources of collagen were used: human placental collagen (Sigma, Type IV) and Bovine achilles tendon collagen (Worthington Biochemicals). The latter substrate was heated for 2 minutes at 100° C. to denature the collagen.

For human placental collagen hydrolysis, reaction mixtures contained 2.0 mg of collagen per ml of Tris-HCl buffer (pH 7.5) containing 0.1 mM $CaCl_2$. Ten azocasein units of each test enzyme were added to each reaction mixture, pre-equilibrated at 37° C. Collagenase (0.14 mg/ml) was also added to a reaction mixture. Samples were removed periodically, and free amino acids and small peptides were determined by the ninhydrin assay procedure described earlier.

Figure 3:
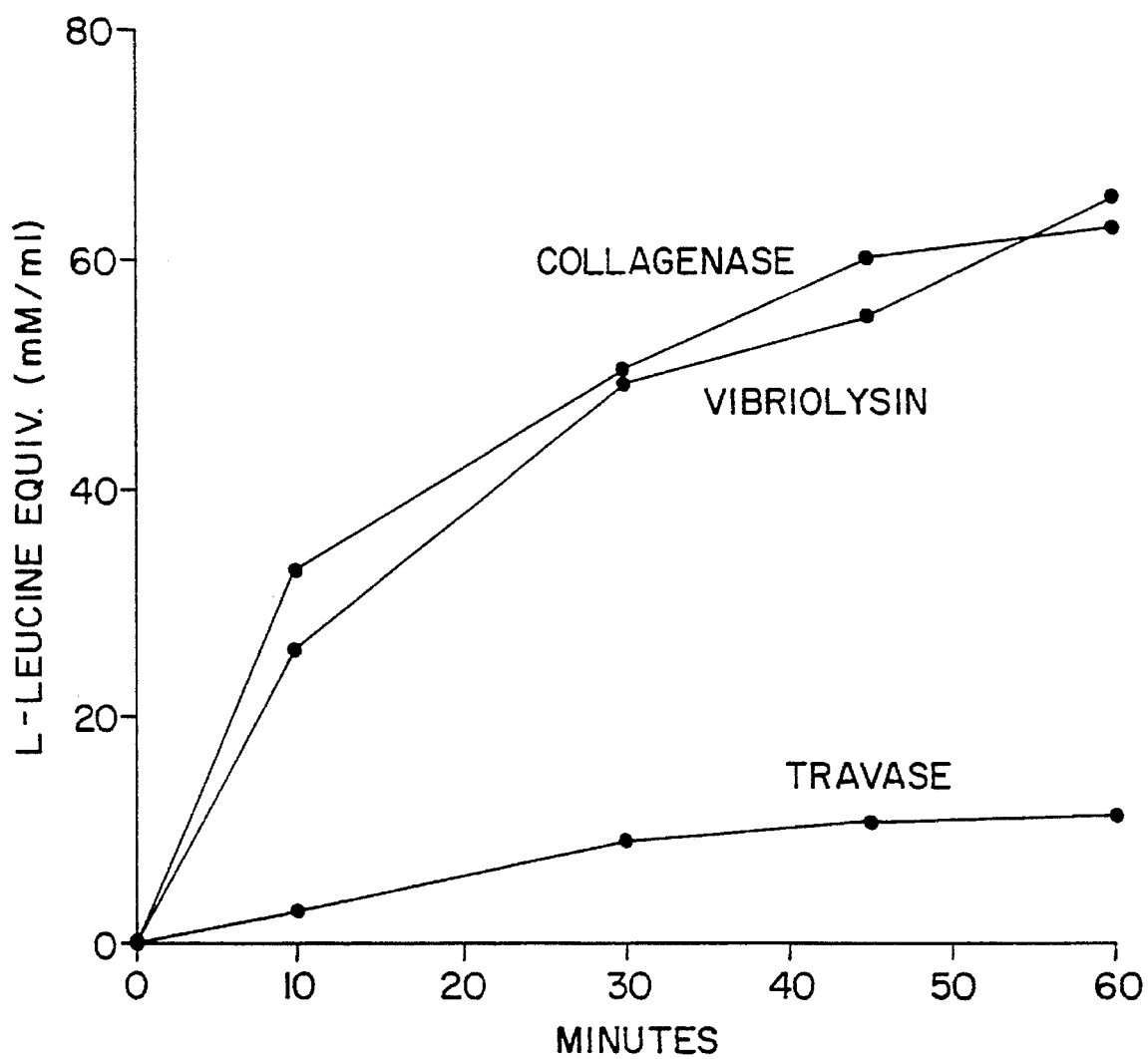
FIG. 3 compares the ability of vibriolysin, Travase, and collagenase to act on the substrate denatured collagen.

The hydrolysis of human placental collagen by vibriolysin and Travase proteases are shown in FIG. 3. The data indicate that vibriolysin exhibits superior collagen hydrolytic activity as compared to Travase proteases and is comparable in activity to collagenase.

For denatured Achilles tendon collagen hydrolysis, reaction mixtures contained 10 mg of collagen per ml of 100 mM TES buffer (pH 7.5) containing 0.9% NaCl and 0.1 mM $CaCl_2$. Five azocasein units per ml of each protease were added to reaction solutions preincubated at 37° C.; 0.1 mg of Worthington collagenase (CLSIII) was also used. The hydrolysis of collagen was determined as a function of time with the ninhydrin assay procedure described earlier. These results are summarized in Table I.

TABLE I

| Enzyme | Leucine (mM) Equivalents Liberated at Minute: | | | | |
|---|---|---|---|---|---|
|  | 0 | 20 | 45 | 60 | 120 |
| Vibriolysin | 0 | 10.4 | 12.4 | 16.8 | 17.2 |
| Travase | 0 | 3.5 | 7.9 | 8.6 | 13.1 |
| Collagenase | 0 | 7.1 | 8.9 | 11.9 | 21.2 |

As noted above, vibriolysin exhibits exceptional activity toward collagen as compared to Travase proteases and digestion of collagen was comparable for collagenase and vibriolysin. The enzyme of the present invention is a more favorable therapy for burn or ulcer treatment due to its effectiveness in breaking down collagen fibers which make up tenacious devitalized wound tissue.

EXAMPLE 4

Elastin Hydrolysis

Elastin represents a minor component of human skin (3%). Hydrolysis of this substrate was determined with reaction solutions containing 6.6 mg of elastin-congo red (Sigma) per ml of 100 mM TES buffer (pH 7.5) containing 0.9% NaCl and 0.1 mM $CaCl_2$. Enzymes (vibriolysin and Travase) were added to reaction solutions (37° C.) to a concentration of 5 azocasein units per milliter; 0.75 ml samples were removed periodically, added to 0.5 ml of 0.7M Sorensons buffer (pH 6.0) and immediately centrifuged. The absorbance of the supernatants were measured at 495 nm.

Figure 4:
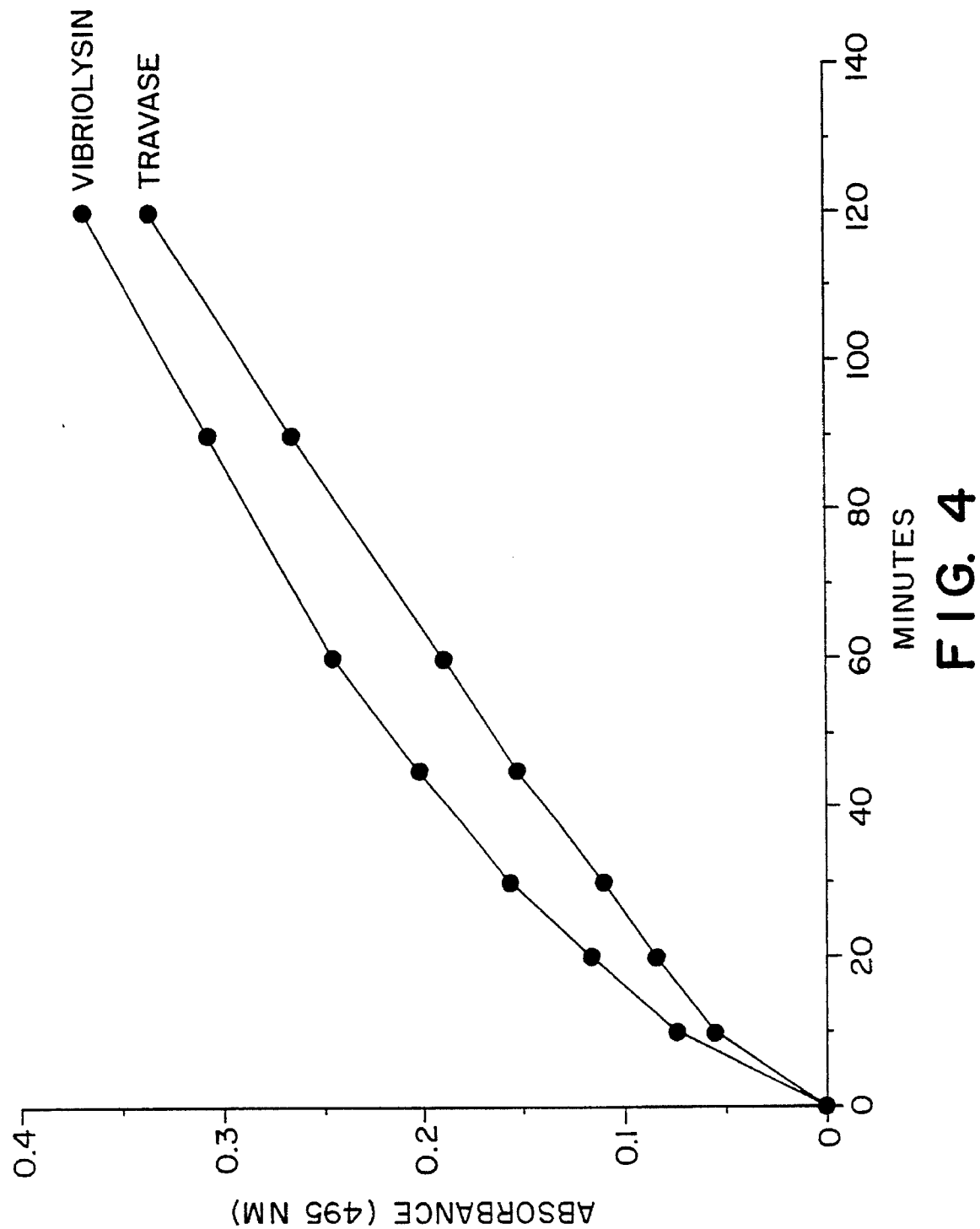
FIG. 4 compares the ability of vibriolysin and Travase to act on the substrate elastin.

The hydrolysis of elastin is shown in FIG. 4. Again, vibriolysin hydrolyses this component of necrotic tissue slightly better than Travase proteases on an equal unit basis.

EXAMPLE 5

Shelf-Life Stability at Ambient Temperature

The shelf-life stability for vibriolysin blended into a hydrophobic and hydrophilic ointment was assessed at ambient temperature (~25° C.). Vibriolysin powder was blended to a concentration of 1,200 azocasein units per gram base into (1) a parafin-mineral oil base (hydrophobic) and (2) a petrolatum-propylene glycol-water base (hydrophilic). Since Travase is formulated in a hydrophobic ointment, one part of this material was mixed with one part of a hydrophilic ointment to attempt to partially simulate the hydrophilic conditions for vibriolysin.

Vibriolysin was extracted from the hydrophobic ointment as described in the USP method for extracting Travase proteases. The hydrophilic formulation was extracted directly with TES buffer. The residual proteolytic activity was then determined by hydrolysis of azocasein.

Figure 5:
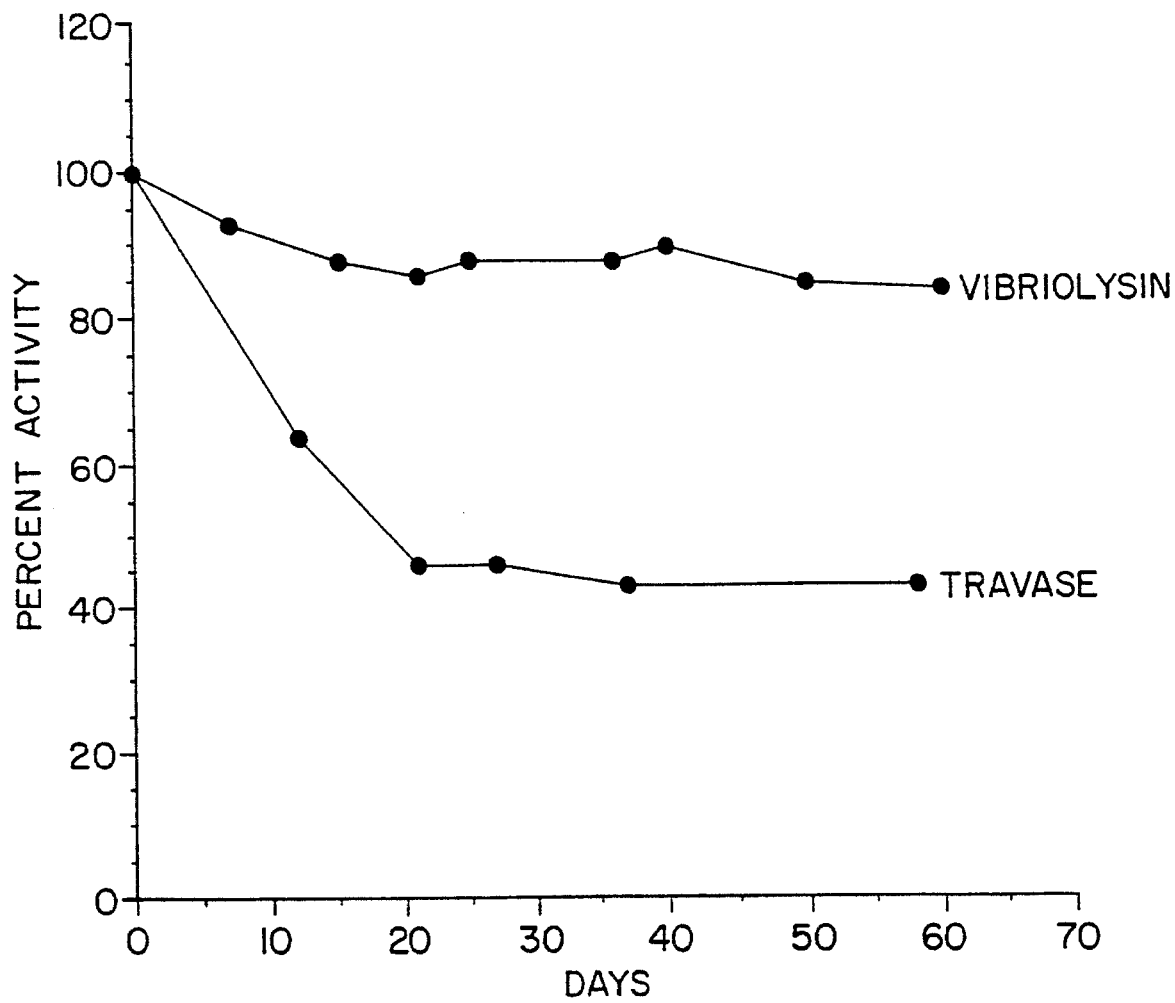
FIG. 5 compares the shelf-life stability at 25° C. of a hydrophilic vibriolysin formulation and a hydrophilic/hydrophobic Travase formulation.

The shelf-life stability of vibriolysin in a hydrophilic base at ambient temperature, as well as the residual activity of Travase proteases in the hydrophobic-hydrophilic composite is shown in FIG. 5. The results indicate that vibriolysin has excellent stability (>80% residual activity) over the 60-day incubation period. By comparison, proteases from the Travase formulation maintained only 43% of its original activity. Both enzymes exhibited comparable shelf-life stability for a hydrophobic base at ambient temperature.

EXAMPLE 6

In Vivo Study

For in vivo assessment of the debriding properties of the protease of this invention, white domestic pigs were selected due to their morphologic and functional similarities of their skin to human skin. Accordingly, one young specific pathogen free (SPF) pig weighing 15–20 kg was kept for two weeks prior to initiating the experiment. The animal was fed a basal diet ad libitum and housed individually in animal facilities with controlled temperature (19°–21° C) and light (12h/12h LD). The experimental animal was prepared, anesthetized and 96 burn wound were made on the exterior two-thirds of the animal as described by Mertz et al. [*Journal Surgical Research* (1990), 48:245–248]. Burn wounds were divided into four treatment groups and evaluated at specific time intervals during a six-day period. Burn wounds were assigned to one of the following treatment groups: (1) Vibriolysin in Silvadene™ cream (Marion) (1,200 units per g), (2) Travase ointment (1,200 units per g), (3) Silvadene cream control, (4) no treatment control. All treatment groups were covered with Tegadermʋ polyurethane dressing which is gas permeable, clear and provides a barrier to external microbial attack. Treatments were immediate or delayed in order to assess prevention of eschar formation and debridement of hardened eschars (96 hours post-burn), respectively.

For the control groups of this experiment, burn wounds that did not receive any treatment formed relatively hard eschars after four days whereas Silvadene cream treatment of burn wounds resulted in slightly softer eschar.

Travase ointment treatment of burn wounds treated on days 1, 2, and 3 developed a concave configuration which was evident upon palpation. In addition, erythema was noted around the wounds throughout the 6-day treatment period. These results suggest that Travase treatment increased the depth of necrosis and was irritating the surrounding skin. These observations are consistent with those of Zawacki [*Surgery* (1974) 77:132] who showed that Travase not only destroyed marginally viable cells but actually deepened the level of injury in a second-degree burn. Eschars of burns treated on the latter days of the experiment (after eschar development) did begin to soften and dissolve necrotic tissue within 24 hours of treatment. However, erythema was noted.

Vibriolysin prevented significant eschar formation of burn wounds receiving treatment immediately after wounding. Unlike Travase treatment, which resulted in a deepening of the wounds, vibriolysin ointment did not hydrolyze viable tissue components. Most significantly, vibriolysin treated wounds exhibited wound contracture as indicated by smaller eschar size. Treatment of burns on days 4, 5, and 6 (after eschar development) caused the eschars to soften and dissolve within 24 hours, as evidenced by softening of wound surfaces, the volume of fluid generated, and the absence of fibrin crust formation. A light erythema was noted for only one treatment period —4 days post burn. Thus, the enzyme of the invention, unlike other such enzyme products, is an effective debriding agent that encourages wound healing.

We claim:

1. A wound treating composition comprising at least one pharmaceutically acceptable carrier admixed with a wound treating effective amount of a protease selected from the group consisting of:
   (a) an extracellular neutral protease produced by cultivation of a *Vibrio proteolyticus* strain, said protease characterized by the following properties:
      i. hydrolyses components of necrotic tissue including denatured collagen, elastin, and fibrin;
      ii. does not substantially hydrolyze native tissue in vivo; and
      iii. exhibits about 80% to about 95% activity when stored at 25° C. in a topical formulation for at least 60 days;
   (b) a neutral protease expressed by recombinant host cells which have been transformed or transfected with an expression vector which provides for the expression of said protease (a);
   (c) fragments of (a) or (b) which exhibit protease activity and are suitable for in vivo administration;
   (d) mutants of the extracellular neutral pro tease of (a) or (b) which comprise a substitution of a single amino acid at a predetermined site in said protease and which exhibit protease activity and are suitable for in vivo administration; and
   (e) mutants of the extracellular protease of (a) or (b) which are produced by chemical or radiation induced mutagenesis and which exhibit protease activity and are suitable for in vivo administration.

2. The composition of claim 1 which is useful for debriding wounds.

3. The composition of claim 1 which is useful for promoting wound healing.

4. The composition of claim 3 which is useful for preventing or treating surgical adhesions.

5. The composition of claim 1 wherein said protease has the amino acid sequence encoded by DNA sequence (SEQ ID NO. 1) as illustrated in FIG. 1.

6. The composition of claim 1 which is suitable for topical administration.

7. The composition of claim 1 wherein said carrier is hydrophobic.

8. The composition of claim 1 wherein said carrier is hydrophilic.

9. The composition of claim 1 which further comprises antibiotics.

10. The composition of claim 3 wherein the protease is further characterized by the ability to effect wound contracture.

11. A method of debriding wounds comprising administering to a wound an effective amount for debriding wounds of the composition of claim 1.

12. The method of claim 11 wherein said wound is a burn.

13. A method for healing wounds comprising administering to a wound an effective amount for healing wounds of the composition of claim 1.

14. The method of claim 11 wherein said wound is a burn.

15. A method for preventing or treating surgical adhesion comprising administering to a wound an effective amount of the composition of claim 1.

16. The wound treating composition of claim 1 wherein the extracellular neutral protease is an extracellular neutral protease as set forth in (a).

17. The wound treating composition of claim 1 wherein the extracellular neutral protease is an extracellular neutral protease as set forth in (b).

18. The wound treating composition of claim 1 wherein the extracellular neutral protease is a fragment as set forth in (c).

19. The wound treating composition of claim 18 wherein said fragment consists of a fragment of the amino acid sequence encoded by the DNA sequence of SEQ ID No:1, as illustrated in FIG. 1.

20. The wound treating composition of claim 1 wherein the extracellular neutral protease is a mutant as set forth in (d).

21. The wound treating composition of claim 20 wherein said mutant is a mutant of the neutral protease having the amino acid sequence encoded by the DNA sequence of SEQ ID No:1, as illustrated in FIG. 1.

22. The wound treating composition of claim 1 wherein the extracellular neutral protease is a mutant as set forth in (e).

23. A method for removing necrotic tissue from a wound comprising contacting said wound with an effective amount for removing necrotic tissue of a protease selected from the group consisting of:

(a) an extracellular neutral protease produced by cultivating of a *Vibrio proteolyticus* strain, said protease characterized by the following properties:
  i. hydrolyses components of necrotic tissue including denatured collagen, elastin, and fibrin;
  ii. does not substantially hydrolyze native tissue in vivo; and
  iii. exhibits about 80 to about 95% activity when stored at 25° C. in a topical formulation for at least sixty days;

(b) a neutral protease expressed by recombinant host cells which have been transformed or transfected with an expression vector which provides for the expression of said protease (a);

(c) fragments of (a) or (b) which exhibit protease activity and are suitable for in vivo administration;

(d) mutants of the neutral protease of (a) or (b) which comprise a substitution of a single amino acid at a predetermined site in the protease and which exhibit protease activity and are suitable for in vivo administration; and (e) mutants of the extracellular protease of (a) or (b) which are produced by chemical or radiation induced mutagenesis and which exhibit protease activity and are suitable for in vivo administration.

24. The method of claim 23 wherein said wound is a burn.

25. The method of claim 23 wherein said protease has the amino acid sequence encoded by DNA sequence (SEQ ID NO. 1 as illustrated in FIG. 1.

26. The method of claim 23 wherein said protease is admixed with at least one pharmaceutically acceptable carrier prior to being administered.

27. A method for enhancing wound healing comprising administering to a wound a therapeutically effective amount for enhancing wound healing of a protease selected from the group consisting of:

(a) an extracellular neutral protease produced by cultivation of a *Vibrio proteolyticus* strain, said protease characterized by the following properties:
  i. hydrolyses components of necrotic tissue including denatured collagen, elastin, and fibrin;
  ii. does not substantially hydrolyze native tissue in vivo; and
  iii. exhibits about 80% to about 95% activity when stored at 25° C. in a topical formulation for at least 60 days;

(b) a neutral protease expressed by recombinant host cells which have been transformed or transfected with an expression vector which provides for the expression of said protease (a);

(c) fragments of (a) or (b) which exhibit protease activity and are suitable for in vivo administration;

(d) mutants of the extracellular neutral protease of (a) or (b) which comprise a substitution of a single amino acid at a predetermined site in said protease and which exhibit protease activity and are suitable for in vivo administration; and (e) mutants of the extracellular protease of (a) or (b) which are produced by chemical or radiation induced mutagenesis and which exhibit protease activity and are suitable for in vivo administration.

28. The method of claim 27 wherein said protease is applied topically to the wound.

29. The method of claim 27 wherein said wound is a burn.

30. The method of claim 27 wherein said wound is a surgical wound.

31. The method of claim 30 which prevents or treats surgical adhesions.

32. The method of claim 27 wherein said protease has the amino acid sequence encoded by DNA sequence (SEQ ID NO. 1) as illustrated in FIG. 1.

33. The method of claim 27 wherein said protease is admixed with at least one pharmaceutically acceptable carrier prior to being administered.

34. The method of claim 27 wherein said protease is applied topically to the wound.

35. The method of claim 31 wherein said protease is injected or implanted into said surgical wound.

36. A method for hydrolyzing burn eschar comprising administering to burned tissue a therapeutically effective amount for hydrolyzing burn eschar of a protease selected from the group consisting of:

(a) an extracellular neutral protease produced by cultivation of a *Vibrio proteolyticus* strain, said protease characterized by the following properties:
  i. hydrolyses components of necrotic tissue including denatured collagen, elastin, and fibrin;
  ii. does not substantially hydrolyze native tissue in vivo; and
  iii. exhibits about 80% to about 95% activity when stored at 25° C. in a topical formulation for at least 60 days;

(b) a neutral protease expressed by recombinant host cells which have been transformed or transfected with an expression vector which provides for the expression of said protease (a);

(c) fragments of (a) or (b) which exhibit protease activity and are suitable for in vivo administration;

(d) mutants of the extracellular neutral protease of (a) or (b) which comprise a substitution of a single amino acid at a predetermined site in said protease and which exhibit protease activity and are suitable for in vivo administration; and (e) mutants of the extracellular protease of (a) or (b) which are produced by chemical or radiation induced mutagenesis and which exhibit protease activity and are suitable for in vivo administration.

37. The method of claim 36 wherein said protease has the amino acid sequence encoded by DNA sequence (SEQ ID NO. 1) as illustrated in FIG. 1.

38. The method of claim 36 wherein said protease is admixed with at least one pharmaceutically acceptable carrier prior to being administered.

39. The method of claim 36 wherein said protease is applied topically to the burned tissue.

\* \* \* \* \*